United States Patent [19]

Inouye et al.

[11] Patent Number: 5,405,775
[45] Date of Patent: Apr. 11, 1995

[54] RETRONS CODING FOR HYBRID DNA/RNA MOLECULES

[75] Inventors: Masayori Inouye; Sumiko Inouye, both of Bridgewater, N.J.

[73] Assignee: The University of Medicine and Dentistry of New Jersey, Piscataway, N.J.

[21] Appl. No.: 518,749

[22] Filed: May 2, 1990

Related U.S. Application Data

[63] Continuation-in-part of Ser. No. 315,432, Feb. 24, 1989, abandoned, Ser. No. 315,427, Feb. 24, 1989, Pat. No. 5,079,151, Ser. No. 315,316, Feb. 24, 1989, Pat. No. 5,320,958, and Ser. No. 517,946, May 2, 1990.

[51] Int. Cl.$^6$ .................. C12N 1/21; C12N 15/70; C12N 15/52
[52] U.S. Cl. .................. 435/252.33; 435/320.1; 536/23.2; 536/25.2
[58] Field of Search .................. 536/27, 33.1, 35.2, 536/23.2, 25.2; 435/91, 172.3, 172.1, 252.3, 252.33, 320.1

[56] References Cited

PUBLICATIONS

Masui et al., "Multipurpose Expression Cloning Vehicles in *Escherichia coli*", in *Experimental Manipulation of Gene Expression*, Academic Press, New York, 1983, Inouye, ed., pp. 15–32.

ATCC Catalog (1985), pp. 66–79.
Yee et al. Multicopy Single-Stranded DNA Isolated from a Gram-Negative Bacterium . . . etc. Cell 38, pp. 203–209 (1984).
Dhundale et al. Distribution of Multicopy Single-Stranded DNA amoung Myxobacterial and Related Species J. Bacteriol. 164, pp. 914–917 (1985).
Furuichi T. et al. Biosynthesis and Structure of Stable Branched RNA Covalently . . . etc. Cell 48, pp. 55–62 (1987).
Dhundale et al. Structure of msDNA from M. xanthus . . . etc. Cell 51, pp. 1105–1112 (1987).
Dhundale et al. Mutations that Affect Production of Branched RNA-Linked msDNA M. xanthus . . . etc. J. Bacteriol., pp. 5620–5624 (1988).
Lim and Maas, Reverse Transcriptase-Dependent Synthesis of a Covalently Linked . . . etc. Cell 56, pp. 891–904 (Mar. 1989).

*Primary Examiner*—Richard A. Schwartz
*Assistant Examiner*—James Ketter
*Attorney, Agent, or Firm*—Weiser & Associates

[57] ABSTRACT

A multicopy single-stranded DNA (msDNA) synthesizing system in *E. coli* is disclosed. The use of the msDNA system to synthesize cDNA in vivo is disclosed. Construction of synthetic msDNA is also disclosed. Also processes for gene amplification and for producing a stable RNA are disclosed.

29 Claims, 17 Drawing Sheets

A

5'CTAGTGATATGTTCATAAACACGCATGTAGGCAGATTCTAGATTGGTTGTGAATCGGCAACCAGTGCCTTATGGCAGGAGCCGCGGGATCACCTACCATCC
3'ACTATACAAGTATTTGTGCGTACATCCGTCTAAGATCTAACCAACACTTAGCGTTGGTCACCGGAATACCGTCCTCGGCGCCCTAGTGGATGGTAGG
                                          XbaI                                        SacII

CTAATATTCTCTTTCAGAGAATATATTAGGTAGGGCAGGTGTGCTCGAGGCGAAGGAGTGCCTGCATGGCGTTCTCCTTGGCCTTTTTCCTCTGGGAA 3'
GATTATAAGAGAAAGTCTCTTATATAATCCATCCCGTCCACACGAGCTCCGCTTCCTCACGGACGTACCGCAAAGAGGAACCGGAAAAAGGAGACCCTTGATC 5'
                              XhoI

B

5' GGGCCTCCCTAAAATCCTTGATTCAGAGCTATACGGGCAGGTGTGC 3'
ms-C1   3' CGCCCGGAGGGATTTTAGGAACTAAGTCTCGATATGCCGTCCACACGAGCT 5'
ms-C2

```
TGG CCA TTC AGA TAC GGA TTT TCA CTT CCT TGA CAG TGC ATG ACT ATG CTG CAT GAA ATC  60

GCA TGA TCG ATT GAG GAT CGT CTT TGC TCA GAT CCG CCA GAA CTG GCG GGC TTT TGC TCA  120

TGT CAT GCA TGT GCA TGA AAA CCA CTG CAT AAA GCG GGC AGG CCT GGC GGG GAT ACG AGC  180

GCG CGC TAT CAC CGA AAA TAG CCA AAA TAC TTC TGG AAA ACA GAA AGT TGA ACT GAT ATC  240
         ⇒RNA    a2
TTC ATA AAC ACG CAT GTA GCC AGA TTT GTT GGT TGT GAA TCG CAA CCA GTG GCC TTA ATG  300
AAG TAT TTG TGC CTA CAT CCG TCT AAA CAA CCA ACA CTT AGC CTT GGT CAC CGG AAT TAC

GCA GGA GGA ATC GCC TCC CTA AAA TCC TTG ATT CAG AGC TAT ACG GCA GGT GTG CTG TGC  360
CGT CCT CCT TAG CGG AGG GAT TTT AGG AAC TAA GTC TCG ATA TGC CGT CCA CAC GAC ACG
            a1
GAA GGA CTG CCT GCA TGC GTT TCT CCT TGG CCT TTT TTC CTC TGG GAT GAA GAA GAA ATG  420
CTT CCT CAC GGA CGT ACG CAA AGA GGA ACC GGA AAA AAG GAG ACC CTA CTT CTT CTT TAC
                                                                              K
 ⇐ DNA
ACA AAA ACA TCT AAA CTT GAC GCA CTT AGG GCT GCT ACT TCA CGT GAA GAC TTG GCT AAA  480
 T   K   T   S   K   L   D   A   L   R   A   A   T   S   R   E   D   L   A   K

ATT TTA GAT ATT AAG TTG GTA TTT TTA ACT AAC GTT CTA TAT AGA ATC GGC TCG GAT AAT  540
 I   L   D   I   K   L   V   F   L   T   N   V   L   Y   R   I   G   S   D   N

CAA TAC ACT CAA TTT ACA ATA CCG AAG AAA GGA AAA GGG GTA AGG ACT ATT TCT GCA CCT  600
 Q   Y   T   Q   F   T   I   P   K   K   G   K   G   V   R   T   I   S   A   P
                                                    *50

ACA GAC CGG TTG AAG GAC ATC CAA CGA AGA ATA TGT GAC TTA CTT TCT GAT TCT AGA GAT  660
 T   D   R   L   K   D   I   Q   R   R   I   C   D   L   L   S   D   C   R   D

GAG ATC TTT GCT ATA AGG AAA ATT AGT AAC AAC TAT TCC TTT GCT TTT GAG AGG GGA AAA  720
 E   I   F   A   I   R   K   I   S   N   N   Y   S   F   G   F   E   R   G   K
                                                                           *100

TCA ATA ATC CTA AAT GCT TAT AAG CAT AGA GGC AAA CAA ATA ATA TTA AAT ATA GAT CTT  780
 S   I   I   L   N   A   Y   K   H   R   G   K   Q   I   I   L   N   I   D   L
                                  H
AAG GAT TTT TTT GAA AGC TTT AAT TTT GGA CGA GTT AGA GGA TAT TTT CTT TCC AAT CAG  840
 K   D   F   F   E   S   F   N   F   G   R   V   R   G   Y   F   L   S   N   Q

GAT TTT TTA TTA AAT CCT GTG GTG GCA ACG ACA CTT GCA AAA GCT GCA TGC TAT AAT GGA  900
 D   F   L   L   N   P   V   V   A   T   T   L   A   K   A   A   C   Y   N   G
                         *150
```

*FIG. 13A*

```
ACC CTC CCC CAA GGA AGT CCA TGT TCT CCT ATT ATC TCA AAT CTA ATT TGC AAT ATT ATG  960
 T   L   P   Q   G   S   P   C   S   P   I   I   S   N   L   I   C   N   I   M

GAT ATG AGA TTA GCT AAG CTG GCT AAA AAA TAT GGA TGT ACT TAT AGC AGA TAT GCT GAT 1020
 D   N   R   L   A   K   L   A   K   K   Y   G   C   T   Y   S   R  |Y   A   D
                                                                        *200

GAT ATA ACA ATT TCT ACA AAT AAA AAT ACA TTT CCG TTA GAA ATG GCT ACT GTG CAA CCT 1080
 D|  I   T   I   S   T   N   K   N   T   F   P   L   E   M   A   T   V   Q   P

GAA GGG GTT GTT TTG GGA AAA GTT TTG GTA AAA GAA ATA GAA AAC TCT GGA TTC GAA ATA 1140
 E   G   V   V   L   G   K   V   L   V   K   E   I   E   N   S   G   F   E   I

AAT GAT TCA AAG ACT AGG CTT ACG TAT AAG ACA TCA AGG CAA GAA GTA ACG GGA CTT ACA 1200
 N   D   S   K   T   R   L   T   Y   K   T   S   R   Q   E   V   T   G   L   T
                                         *250

GTT AAC AGA ATC GTT AAT ATT GAT AGA TGT TAT TAT AAA AAA ACT CGG GCG TTG GCA CAT 1260
 V   N   R   I   V   N   I   D   R   C   Y   Y   K   K   T   R   A   L   A   H

GCT TTG TAT CGT ACA GGT GAA TAT AAA GTG CCA GAT GAA AAT GGC GTT TTA GTT TCA GGA 1320
 A   L   Y   R   T   G   E   Y   K   V   P   D   E   N   G   V   L   V   S   G
                                                                            *300

GGT CTG GAT AAA CTT GAG GGG ATG TTT GGT TTT ATT GAT CAA GTT GAT AAG TTT AAC AAT 1380
 G   L   D   K   L   E   G   M   F   G   F   I   D   Q   V   D   K   F   N   N

ATA AAG AAA AAA CTG AAC AAG CAA CCT GAT AGA TAT CTA TTG ACT AAT GCG ACT TTG CAT 1440
 I   K   K   K   L   N   K   Q   P   D   R   Y   V   L   T   N   A   T   L   H

GGT TTT AAA TTA AAG TTG AAT GCG CGA GAA AAA GCA TAT ACT AAA TTT ATT TAC TAT AAA 1500
 G   F   K   L   K   L   N   A   R   E   K   A   Y   S   K   F   I   Y   Y   K
                                 *350

TTT TTT CAT GGC AAC ACC TGT CCT ACG ATA ATT ACA GAA GGG AAG ACT GAT CGG ATA TAT 1560
 F   F   H   G   N   T   C   P   T   I   I   T   E   G   K   T   D   R   I   Y

TTG AAG GCT GCT TTG CAT TCT TTG GAG ACA TCA TAT CCT GAG TTG TTT AGA GAA AAA ACA 1620
 L   K   A   A   L   H   S   L   E   T   S   Y   P   E   L   F   R   E   K   T
                                                                            *400

GAT AGT AAA AAG AAA GAA ATA AAT CTT AAT ATA TTT AAA TCT AAT GAA AAG ACC AAA TAT 1680
 D   S   K   K   K   E   I   N   L   N   I   F   K   S   N   E   K   T   K   Y
                              P

TTT TTA GAT CTT TCT GGG GGA ACT GCA GAT CTG AAA AAA TTT CTA GAG CGT TAT AAA AAT 1740
 F   L   D   L   S   G   G   T   A   D   L   K   K   F   L   E   R   Y   K   N
```

*FIG. 13B*

```
AAT TAT GCT TCT TAT TAT GCT TCT GTT CCA AAA CAC CCA GTG ATT ATG CTT CTT GAT AAT  1800
 N   Y   A   S   Y   Y   G   S   V   P   K   Q   P   V   I   M   L   L   D   N
                                    *450

GAT ACA GCT CCA AGC GAT TTA CTT AAT TTT CTG CGC AAT AAA GTT AAA AGC TGC CCA GAC  1860
 D   T   G   P   S   D   L   L   N   F   L   R   N   K   V   K   S   C   P   D

GAT GTA ACT GAA ATG AGA AAG ATG AAA TAT ATT CAT CTT TTC TAT AAT TTA TAT ATA CTT  1920
 D   V   T   E   N   R   K   N   K   Y   I   H   V   F   Y   N   L   Y   I   V
                                                                    *500

CTC ACA CCA TTG AGT CCT TCC GGC GAA CAA ACT TCA ATG GAG GAT CTT TTC CCT AAA GAT  1980
 L   T   P   L   S   P   S   G   E   Q   T   S   N   E   D   L   F   P   Q   D

ATT TTA GAT ATC AAG ATT GAT GGT AAG AAA TTC AAC AAA AAT AAT GAT GGA GAC TCA AAA  2040
 I   L   D   I   K   I   D   G   K   K   F   N   K   N   N   D   G   D   S   K

ACG GAA TAT GGG AAG CAT ATT TTT TCC ATG AGG GTT GTT AGA GAT AAA AAG CGG AAA ATA  2100
 T   E   Y   G   K   H   I   F   S   N   R   V   V   R   D   K   K   R   K   I
                                    *550

GAT TTT AAG GCA TTT TGT TGT ATT TTT GAT GCT ATA AAA GAT ATA AAG GAA CAT TAT AAA  2160
 D   F   K   A   F   C   C   I   F   D   A   I   K   D   I   K   E   H   Y   K

TTA ATG TTA AAT AGC TAA TGA ACA GCC CTA ACG TTA TGA ACG CTA AGG CTG ATT TTT CGT  2220
 L   M   L   N   S

TAA AAT TTA TAT GCT TTG AAT TGT AAT ATA TTA TCT TCA AGC CAT TTA TTT AAT TCC TGC  2280

ATC CTT TTC TCT AAG GGT ATT AAT TCG TTC CTC ACA AAC ACT AAA CTC GCT TTT TCC ACA  2340

TCC CCA AAC CCC CCT AAC ATT ATT CGG CAT AAT CCC CAT CAT TTG CGG TGG CAC ACC ATG  2400

CGC TGC CAT CAT CTC ATC GCG GC
```

*FIG. 13C*

RETRONS CODING FOR HYBRID DNA/RNA MOLECULES

This is a continuation-in-part of patent application Ser. No. 07/315,432, filed Feb. 24, 1989, now abandoned, by Lampson et al. and also of two patent applications co-filed on even date, Feb. 24, 1989, U.S. Ser. No. 07/315,427, now U.S. Pat. No. 5,079,151, U.S. Ser. No. 07/315,316 now U.S. Pat. No. 5,320,958 and U.S. Ser. No. 07/517,946, filed May 2, 1990 and relates to a pending patent application filed May 2, 1990, entitled "Prokaryotic Reverse Transcriptase" by Masayori Inouye and Sumiko Inouye which are incorporated herein by reference.

The parent application discloses the presence of msDNA in the clinical E. coli isolate, Cl-1, the cloned Petton from the same strain and its nucleotide sequence. The instant continuation-in-part application additionally discloses a retron from another E. coli clinical isolate, Cl-23, a process for in vivo cDNA production in E. coli and synthetic msDNA molecules. Additional disclosures of processes for gene amplification and production of stable RNA are also made. Large production of proteins is made possible by the invention.

FIELD OF THE INVENTION

This invention relates to a prokaryotic msDNA (multicopy single-stranded DNA) synthesizing system, also known as the retron. The invention also relates to msDNAs and to their production and their use to synthesize cDNA. The invention further relates to the use of one or more retron components in the production of various msDNAs.

BACKGROUND OF THE INVENTION

A novel satellite DNA called msDNA (multicopy single-stranded DNA) was originally found in Myxococcus xanthus, a Gram-negative bacterium living in soil (1). It consists of a 162-base single-stranded DNA, the 5' end of which is linked to a branched RNA (msdRNA) of 77 bases by a 2',5'-phosphodiester linkage at the 2' position of the 20th rG residue (2). There are approximately 700 copies of msDNA per genome. msDNA is widely distributed among various myxobacteria including the closely related Stigmatella aurantiaca which possesses an msDNA, msDNA-Sa163. This molecule is highly homologous to msDNA-Mx162 from M. xanthus (3, 4). It is noteworthy that several M. xanthus strains, independently isolated from different sites, all contain msDNA (5). Recently it was found that M. xanthus contains another smaller species of msDNA called msDNA-Mx65 (6). In contrast to the close homology between msDNA-Mx162 and msDNA-Sa163, there is no primary sequence homology between msDNA-Mx162 and the small molecule, msDNA-Mx65. However, it was found that msDNA-Mx65 does share key secondary structures such as a branched rG residue, a DNA-RNA hybrid at the 3' ends of the msDNA and msdRNA, and stem-loop structures in RNA and DNA strands.

It has been further shown that msdRNA is derived from a much longer precursor RNA (pre-msdRNA), which can form a very stable stem-and-loop structure (2). A novel mechanism for msDNA synthesis was proposed, in which the stem-and-loop structure of pre-msdRNA serves as a primer for initiating msDNA synthesis as well as a template to form the branched RNA-linked msDNA, and predicted that a reverse transcriptase (RT) is required for this reaction (2).

Initial studies indicated that msDNA is not found in the common E. coli K-12 laboratory strain (1). To date, it has been observed that approximately 6% of all E. coli isolates from clinical strains carry an msDNA synthesizing system. This synthesizing system has been classified as a retron on the basis of rather surprising similarities between the msDNA and retroviruses and retrotransposons (8).

The present invention provides for an E. coli msDNA synthesizing system. The invention also provides for its products and uses.

BACKGROUND ART

Bacterial reverse transcriptase and msDNA were initially discovered in Myxococcus xanthus and another myxobacterium Stigmatella aurantiaca. The publications noted here report on the myxobacteria discoveries. All such references are hereby incorporated by reference.

Yee, T. and Inouye M. "Reexamination of the Genome Size of Myxobacteria, Including the Use of a New Method for Genome Size Analysis", J. Bacteriol. 145, pp. 1257-1265 (1981), reports the discovery of a rapidly renaturing fraction of DNA found during the study of Myxobacteria genome size.

Yee, T. et al., "Multicopy Single-Stranded DNA Isolated from a Gram-Negative Bacterium, Myxococcus xanthus", Cell 38, pp. 203-209 (1984), reports that the rapidly renaturing DNA found in Myxococcus xanthus is found as a satellite band upon polyacrylamide gel electrophoresis. This satellite DNA was called msDNA. Myxococcus xanthus was found to contain 500 to 700 copies of msDNA per chromosome. The msDNA was cloned and sequenced. Its length and secondary structure was determined. A similar satellite DNA was found in the myxobacterium Stigmatella aurantiaca. The authors report that they were unable to detect any satellite DNA in Escherichia coli K-12.

Furuichi, T. et al., "Branched RNA Covalently Linked to the 5' End of a Single-Stranded DNA in Stigmatella aurantiaca: Structure of msDNA", Cell 48, pp. 47-53 (1987) and Furuichi, T. et al., "Biosynthesis and Structure of Stable Branched RNA Covalently Linked to the 5' End of Multicopy Single-Stranded DNA of Stigmatella aurantiaca", Cell 48 pp 55-62 (1987), showed that msDNA isolated from S. aurantiaca (type Sa163) contained a DNA portion that was linked to an RNA molecule (msdRNA) by a 2', 5'-phosphodiester bond. The authors also reported that the coding region for msdRNA (msr) is located downstream of the coding region for msDNA (msd). The coding regions were found to exist in opposite orientation with respect to each other with their 3' ends overlapping.

Dhundale, A. R. et al., "Distribution of Multicopy Single-Stranded DNA among Myxobacteria and Related Species", J. Bacteriol. 164, pp. 914-917 (1985), examined how widely msDNA exists in various bacteria closely and distantly related to M. xanthus. msDNA was found in other myxobacteria and nine independently isolated strains of M. xanthus. The authors report msDNA to be found in certain gliding bacteria but not in others.

The references cited above do not disclose or suggest that msDNA exists in E. coli. The publication of Yee et al. in Cell 38, 203 (1984) indicates that msDNA was undetectable in E. coli K-12 strain. The present invention encompasses recombinant DNA constructs encoding an *E. coli* msDNA synthesizing system and the components thereof. The unexpected discovery that about 6% of *E. coli* clinical isolates examined to date harbor msDNA enables the present invention. The present invention is thus a novel departure from the background art.

BRIEF DESCRIPTION OF THE FIGURES

FIG. 3 shows the synthetic msDNA genes.

FIG. 12A and 12B show a DNA blot analysis of *E. coli* chromosomal DNA and analysis of msDNA synthesis.

FIG. 13 shows the nucleotide sequence of an msDNA-Ec67 retron.

SUMMARY OF THE INVENTION

Methods and compositions are provided for production of msDNA. The invention enables production of natural and synthetic msDNA.

The invention provides for an msDNA synthesizing system. The three components of this system can be cloned in an *E. coli* expression vector as a unit or separately. The source of these components may be natural or synthetic. The components can also be utilized as they exist on the prokaryotic chromosome.

The method of the invention provides for the utilization of the prokaryotic msDNA synthesizing system. The synthesizing system (retron) has three components, msd, msr and an ORF. Transcription and translation of the ORF region results in production of a protein having reverse transcriptase activity. Transcription of the msr region followed by DNA synthesis by reverse transcriptase results in msDNA production.

The method of the invention provides for cDNA production within the cell. The invention provides an in vivo system to produce cDNA complementary to a specific RNA transcript in *E. coli*. Upon insertion of a sequence complementary to the 3' end of a msDNA molecule into a specific mRNA, cDNA to the mRNA is produced in vivo using msDNA as a primer. It is contemplated that cDNA could also be produced in vitro by providing an appropriate RNA, msDNA and reverse transcriptase.

The invention also contemplates additional uses of artificial retrons as tools in life sciences research. Artificial msDNAs are contemplated to be useful for gene amplification, mRNA stabilization and production of ribozymes and antisense RNAs. Additionally, owing to ease of detection of msDNA, it is contemplated that bacteria producing msDNA can be used for the screening of antibodies and chemicals which block reverse transcriptase activity.

DETAILED DESCRIPTION OF THE INVENTION

Figure 1:
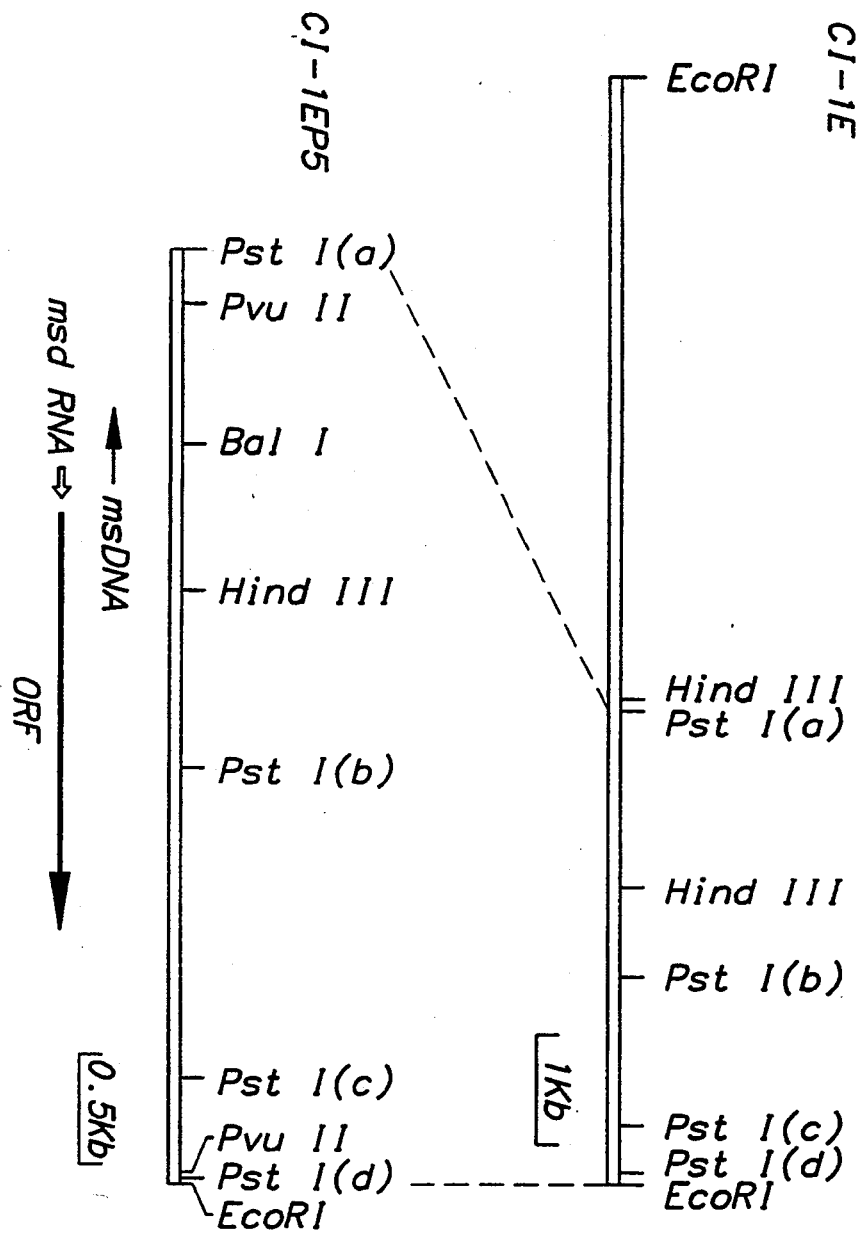
FIG. 1 shows a restriction map of an *E. coli* retron and flanking sequences.

This invention relates to a prokaryotic msDNA synthesizing system. This genetic system has been found in *E. coli* isolated from individuals with blood and urinary tract infections and those that are apparently healthy. The DNA fragment encoding the whole genetic system of msDNA has been classified as a retron since it appears to represent a primitive form of retroelement (8). It is proposed that the function of msDNA in the cell may be to serve as a primer to produce cDNA and the retron may function as a transposable element. FIG. 1 shows a restriction map of the retron. The DNA strand of the msDNA molecule is coded for by the msd gene. The RNA molecule of msDNA is encoded by the msr gene. The two genes are convergently situated (5' to 3') such that their respective 3' ends overlap. The third retron component is an open reading frame (ORF) located upstream of msd and downstream of msr encoding a protein with reverse transcriptase activity (9). It is proposed that other ORFs may exist within the retron. These other ORFs may share sequence similarities with retrovital proteins such as integrase, protease and gag proteins.

A population of *E. coli* clinical strains carry msDNA-synthesizing systems. At present, retrons have been found in approximately 6% (7 out of 113) of the clinical strains analyzed. It is contemplated that retrons exhibiting structural similarities exist in other genera of the Enterobacteriaceae family.

Retrons from two *E. coli* clinical strains have been sequenced. The RNA and DNA sequence of the msDNAs produced by these retrons has also been determined. The complete primary and proposed secondary structure of these molecules (Ec67 and 74) are shown in FIG. 2. The numeric designation indicates the length of the DNA molecule. Little sequence homology is observed in both the RNA and DNA components of these molecules. However, despite their primary sequence differences, *E. coli* msDNAs all share key functional common features which include a single-stranded DNA with a stem-and-loop structure, a single-stranded RNA with a stem-and-loop structure, a 2', 5'-phosphodiester linkage between RNA and DNA, and a DNA-RNA hybrid at the 3' ends.

Figure 4:
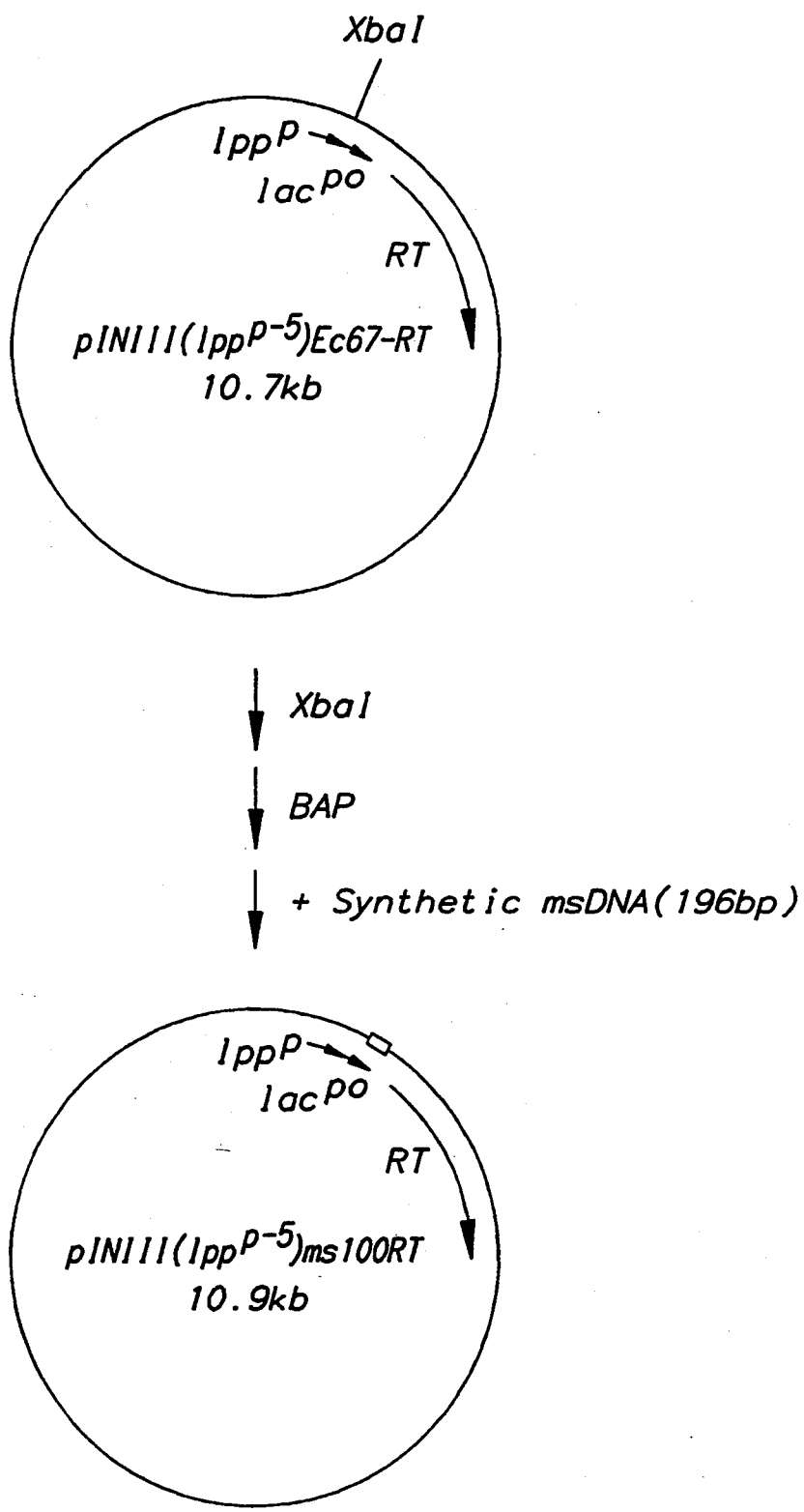
FIG. 4 shows the construction scheme for pI-NIII(lpp$^{p-5}$) ms100-RT.

The invention also relates to the use of retron components in the production of various msDNAs and reverse transcriptases. The retron of the invention can be natural or synthetic. Two entire msr-msd regions have been synthesized using synthetic oligonucleotides and an example is illustrated in FIGS. 3 and 4. The region was inserted into a pINIII vector (14) (as a form of double-stranded DNA) such that a synthetic pre-msdRNA was produced in response to the addition of a lac inducer. The total gene length of approximately 200-bp was constructed by four units of double-stranded oligonucleotides. The gene was inserted into the unique XbaI site of the vector. The RT gene was provided in cis by inserting it into the same plasmid or in trans by inserting it in a separate plasmid. It is thought that the retron can be utilized on the chromosome or extra-chromosomally. It is contemplated that a naturally occurring retron can be altered through genetic engineering techniques.

Figure 8:
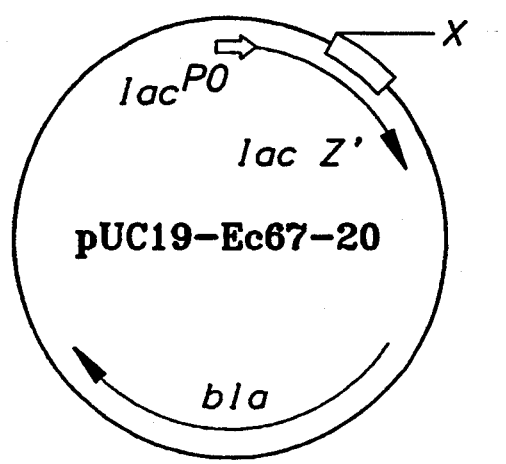
FIG. 8 shows the pUC19 derivative used for in vivo cDNA production, pUC19-Ec67-20mer.

It is proposed that various artificial msDNAs can be constructed within the limitation of the requirements stated above. It is further proposed that the 3' end of msDNA can be variable, this part of the sequence can be substituted with a complementary sequence to a specific mRNA. Such an msDNA may be able to serve as a primer for the production of cDNA for a specific mRNA.

msDNA-Ec67 retron is able to synthesize cDNA if cells contain an mRNA which has a stretch of RNA sequence complementary to the 3' end of msDNA-Ec67. A plasmid was constructed from pUC19 (13) which was able to produce an mRNA containing a sequence complementary to the 5' end of msDNA-Ec67 (FIG. 8). The sequence contained the 15-base sequence identical to the 3' end of msDNA-Ec67 such that the RNA transcript from pUC19 contains the 15-base sequence complementary to the 3' end of msDNA-Ec67 at position 80.

Figure 9:
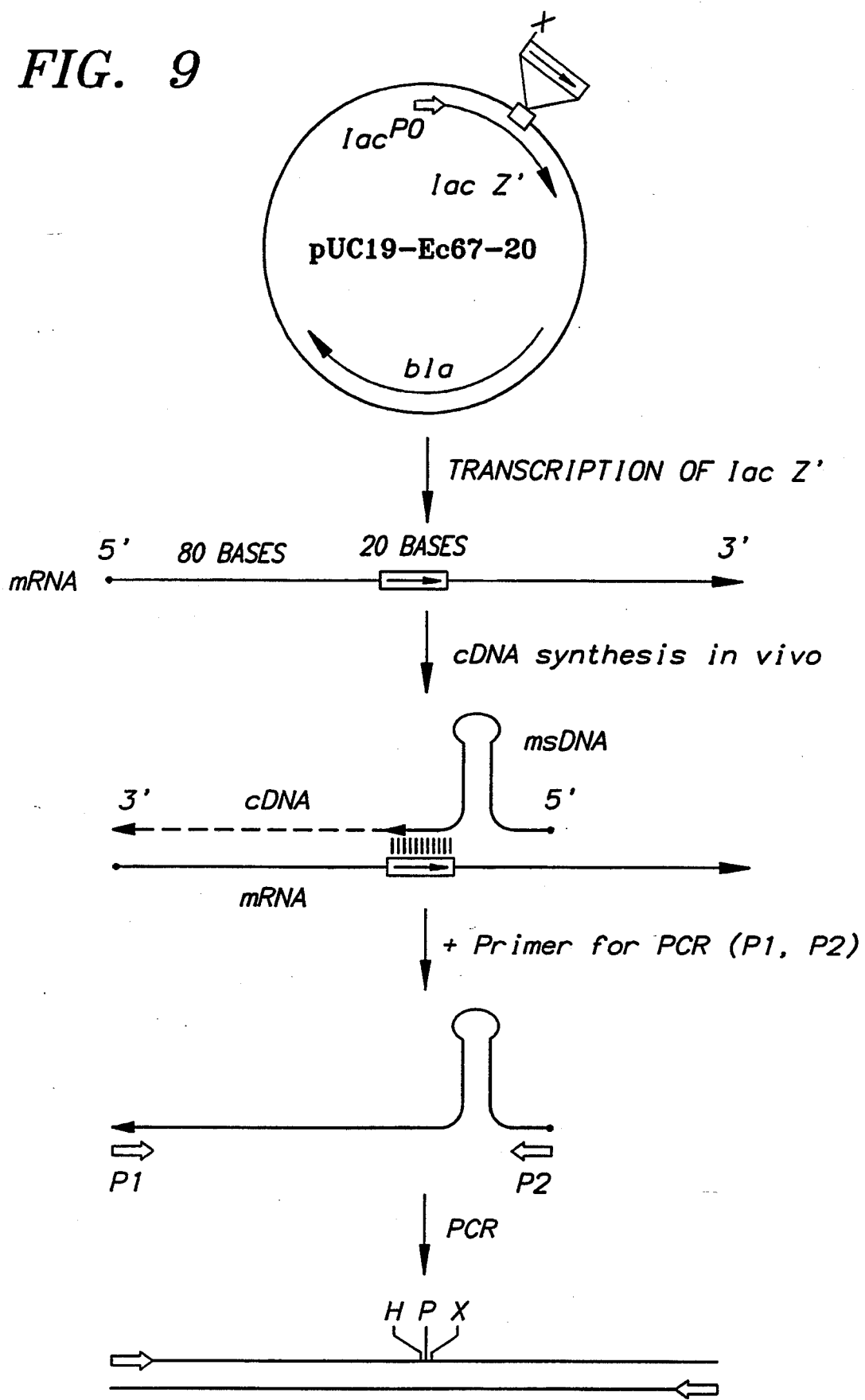
FIG. 9 shows the steps of in vivo cDNA synthesis.
Figure 10:
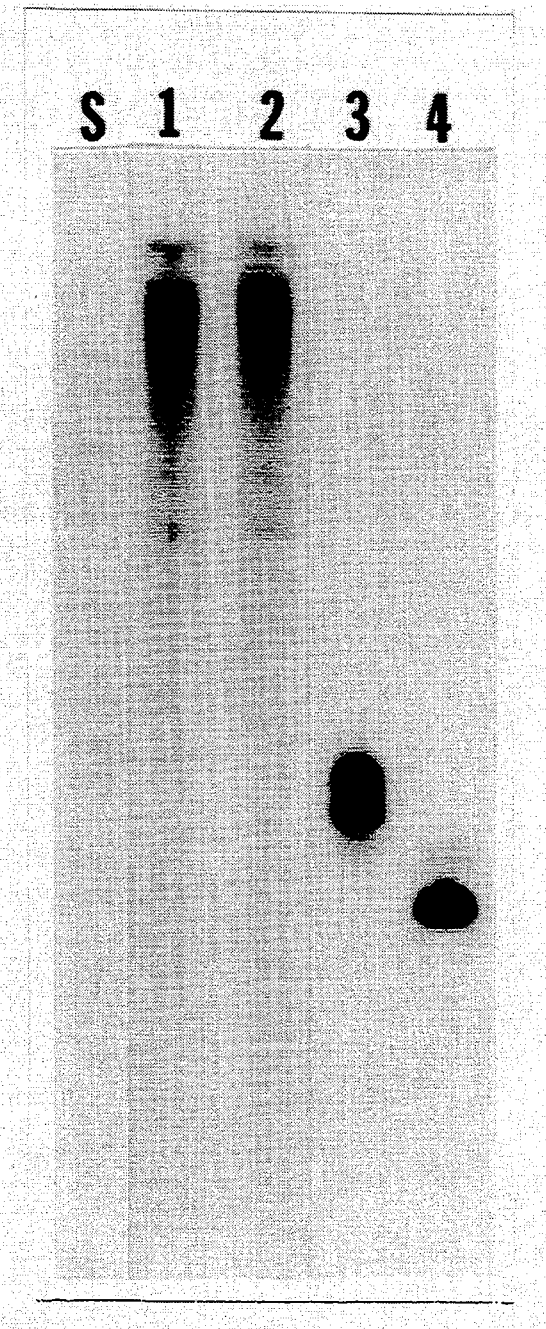
FIG. 10 shows the detection of msDNA in a clinical isolate of *E. coli*.

When E. coli harboring the Ec67 retron capable of synthesizing msDNA-Ec67 is transformed with plasmid pUC19-Ec67-20mer, the 3'-end region of Ec67-msDNA forms DNA-RNA hybrids not only with the 3' end of msdRNA (as shown FIG. 2) but also with the RNA transcript from pUC19-Ec67-20-mer as shown in FIG. 9. Since the cells contain Ec67-RT, this enzyme starts to synthesize cDNA by extending the 3' end of msDNA along the mRNA template. A single-stranded DNA is synthesized of 152 bases which consists of the 67-base msDNA at the 5' end and the 85-base cDNA to the 5' end of the lac transcript at the 3' end. Identification of this cDNA was made by polymerase chain reaction (PCR) (21). The results in FIG. 10A indicated a good agreement with the predicted 150-bp cDNA depicted in FIG. 9. An identical result was obtained with cells transformed with a pINIII vector (14) which also contained the same 20-bp sequence (FIG. 10, lanes 3 and 5).

Figure 11:
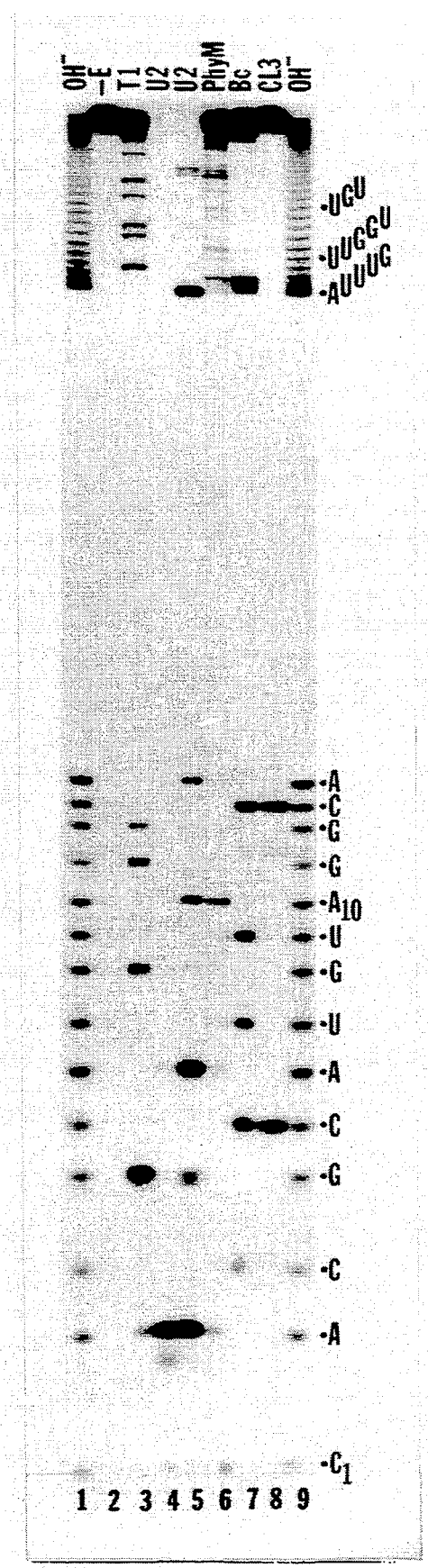
FIG. 11 shows the sequence determination of the branched RNA linked to msDNA.

The results described above are consistent with the cDNA structure depicted in FIG. 9, in which msDNA primes cDNA synthesis. To unambiguously prove this model, the DNA sequence of the PCR product with pUC19-Ec67-20-mer (FIG. 10A, lane 2) was determined. FIG. 11 shows the DNA sequence of the junction site, which clearly demonstrates that the 3' end of Ec67-msDNA is connected to the cDNA of the lac transcript of pUC19 at the 85th position.

The present results unambiguously demonstrate that cDNA to a specific RNA transcript can be synthesized in E. coli cells by the method of the invention. This further indicates that cells are capable of producing cDNA if they contain RT and appropriate primers for a specific template.

cDNA detected in the present study seems to exist mostly as single-stranded DNA, since cDNA production was detected by PCR after RNaseA treatment but not after treatment with S1 nuclease (See Example 5). Conversion of single-stranded cDNA to double-stranded cDNA may, however, easily occur in the cells if appropriate primers are provided. It is contemplated that an msDNA-synthesizing system could be established in eukaryotic cells. It is further contemplated that such a system may be used to obtain cDNA to a specific RNA transcript in vivo or cDNA to polyadenylated mRNAs in vivo by properly engineering the 3' ends of msDNA.

It is also proposed that E. coli RT can synthesize cDNA from an mRNA if an appropriate primer is provided. An mRNA having a stable stem-and-loop structure at the 3' end may be able to prime cDNA synthesis by itself if an RT gene is expressed in the cell.

Another contemplated approach is to use exogenously added synthetic oligonucleotide as primers which are complementary (antisense) to the mRNA. It is proposed that cells permeabilized with organic solvents will be useful for this method.

The system of the invention is useful in various applications. Since msDNA is produced in several hundred copies per retron, the system can be used for gene amplification. This can be achieved by replacing the double-stranded region of msDNA with another double-stranded DNA containing a gene. In the synthetic msDNA depicted in FIG. 5, the stem-and-loop region (double-stranded region) of msDNA can be removed by restriction enzyme digestion of the retron-containing plasmid DNA with XhoI and SacII. A new DNA fragment is then ligated to this site, which contains two copies of a gene of interest either in head-to-head or in tail-to-tail orientation. As a result, when this region is copied as a single-stranded DNA in a synthetic msDNA, a secondary structure or a stem-and-loop structure is formed because of palindromic orientation of the two copies of the gene. Thus, the gene of interest is reconstructed in the stem structure. By this method of gene amplification, a large number of copies of the gene (e.g., more than 4,000), can be produced. This is provided that the plasmid containing msDNA sequences is maintained in E. coli at a copy number of 20 and that each plasmid produces 200 transcripts of the msDNA in a steady state. Of course, since the msDNA structure is not foreign to E. coli, the microorganism is particularly well suited as the vehicle for gene multiplication.

In another application, the msDNA of the system of the invention are used to produce stable RNA. A DNA fragment can be inserted in the XbaI site located in the RNA structure (see FIG. 3A). When the resulting retron is transcribed, RNA from the inserted DNA is added in the XbaI site of msdRNA. When the inserted DNA contains an open-reading frame, then the newly formed msdRNA functions as an mRNA containing the open-reading frame to produce a polypeptide. If the same DNA fragment is inserted in the opposite orientation, the newly synthesized msdRNA contains an RNA sequence complementary to the mRNA. Thus, it works as the antisense RNA against the mRNA, so that it can be used to regulate the expression of the gene for the mRNA. The RNA produced contains a Shine-Dalgarno sequence, an initiation codon and the coding sequence. This mRNA is extremely stable because of the 3' DNA-RNA hybrid structure, the secondary structure of the mRNA at the 3' end, and the branched rG residue at the 5' end. All these structures are considered to protect the mRNA from degradation.

Thus, the invention provides a very useful system whereby a large amount of a specific mRNA is produced in a cell, resulting in expression of a large quantity of a specific polypeptide from the cloned gene. The industrial applications of the system are evident. High volume of a desired peptide can be comparatively inexpensively produced from the corresponding selected gene. Numerous valuable polypeptides can be produced like interferon, erythropoietin, plasminogen activators, antiplatelet aggregants, interlukin, growth and other hormones; and other biologically useful proteins.

Another important application of the invention is that the msDNA be used to construct ribozymes or antisense RNAs or their combination. A DNA fragment can be inserted in the XbaI site so that the msdRNA synthesized from this construct contains a so-called hammerhead structure which works as a ribozyme, i.e., a ribonuclease which cleaves a specific RNA. Such a ribozyme can be used to destroy a specific mRNA. The XbaI site shown in FIG. 3 (see also FIG. 5) can be utilized for this purpose. If a hammerhead structure from a plant viroid (15-17) can be formed in the msdRNA at this site, a ribozyme is formed in msdRNA, which functions as a sequence specific ribonuclease. Similarly, if an antisense RNA against a specific gene is inserted at this site, the msDNA-antisense RNA may be very effective in blocking the expression of a specific gene. It is thought that a better suppression effect may occur upon combination of both ribozyme and antisense RNA within a single msdRNA. This approach leads to a new method for constructing more effective antisense RNA. The ribozyme functions to cleave selected other RNA molecules, e.g., specific vital RNAs. This antiviral approach can be usefully applied to a ribozyme specific as anti-HIV agent. The practical applications are evident in this area.

It is also proposed that E. coli producing msDNA can be used for the screening of antibodies and chemicals which block RT activity. It is thought that anti-RT compounds will show stronger inhibitory effects on msDNA synthesis than on chromosomal DNA synthesis.

The following examples illustrate the detection of msDNA in E. coli, nucleotide sequencing of msDNA and cloning of the msDNA genetic locus. The msDNAs and reverse transcriptases described herein are not limited to those specifically described herein. It can readily be seen by those skilled in the art that various msDNA molecules can be produced through synthetic means or genetic engineering.

The following examples are only given for purposes of illustration and not by way of limitation on the scope of the invention.

EXAMPLE 1

Detection of msDNA in E. coli.

Fifty independent E. coli urinary tract isolates identified with the use of the API-20E identification system (9) were examined for the presence of msDNA. Since msDNA contains a DNA-RNA duplex structure, the 3' end of the DNA molecule serves as an intramolecular primer and the RNA molecule as a template for RT. When RNA prepared from one of the clinical strains, E. coli C1-1, was labeled in this manner, two distinct, low molecular weight bands of about 160 bases became labeled with $^{32}P$ and are shown in FIG. 10. If the labeled sample is digested with ribonuclease (RNase) A prior to loading on the gel, a single band corresponding to 105 bases of single-stranded DNA is detected (lane 4). This indicates that both bands in lane 3 contain a single-stranded DNA of identical size. The two labeled bands observed prior to RNase treatment (lane 3) are due to two species of msDNA comprised of a single species of single-stranded DNA linked to RNA molecules of two different sizes. Among the fifty clinical isolates screened, three other strains produced msDNA-like molecules of varying size and quantity suggesting extensive diversity among these molecules.

In a similar experiment, RNA was extracted from 113 independent clinical isolates. Fifty were from patients with a urinary tract infection, and 63 from patients with blood infections. Among the 50 strains from patients with a urinary tract infection, three were found to contain msDNA. From patients with blood infections, 3 strains were found to contain msDNA. In addition, msDNAs have been found in E. coli strains from apparently normal human stool samples; msDNA was not observed in the E. coli K-12 strain, C600.

EXAMPLE 2

Nucleotide sequence of msDNA.

To determine the base sequence of the DNA molecule, the RNA-DNA complex isolated from the clinical stain was labeled at the 3' end of the DNA molecule with AMV-RT and [α-$^{32}$P]dATP. By adding ddCTP, ddTTP, and ddGTP to the reaction mixture, a single labeled adenine is added to the 3' end of the DNA molecule. RNA is removed with RNase A+T and the end-labeled DNA is subjected to the Maxam and Gilbert sequencing method (3). FIG. 2 shows that this msDNA consists of a single-stranded DNA of 67 bases and that it can form a secondary hair-pin structure. Accordingly, this msDNA has been denoted as msDNA-Ec67.

The sequence of the RNA molecules was determined using the RNA-DNA complex purified from E. coli C1-1 as described in Example 1. As shown in FIG. 11, a large gap is observed in the RNA sequence "ladder". This gap is due to the DNA strand branched at the 2' position of the 15th rG residue of the RNA strand which produces a shift in mobility of the sequence ladder (see FIG. 2). The RNA consists of 58 bases with the DNA molecule branched at the G residue at position 15 by a 2', 5'-phosphodiester linkage. The branched G structure was determined as described for msDNAs from myxobacteria (5, 6). After RNase (A and T$_1$) treatment, msDNA retains a small oligoribonucleotide linked to the 5' end of the DNA molecule due to the inability of RNases to cleave in the vicinity of the branched linkage. The 5' end was labeled with [γ-$^{32}$P] ATP using T$_4$ polynucleotide kinase and the labeled RNA molecule was detached from the DNA strand by a debranching enzyme purified from HeLa cells (5, 6). This small RNA was found to be a tetraribonucleotide which could be digested with RNase T$_1$ to yield a labeled dinucleotide. Since RNase T$_1$ could not cleave the RNA molecule at the G residue before debranching enzyme treatment, it was concluded that the single-stranded DNA is branched at the G residue via a 2', 5'-phosphodiester linkage. In addition, partial RNase U$_2$ digestion cleaved the RNA molecule to yield a $^{32}$P-labeled mono- and a $^{32}$P-labeled trinucleotide. Thus, the sequence of the tetranucleotide is 5'A-G-A-(U or C)3'. Based on these data, the complete structure of msDNA-Ec67 from E. coli C1-1 is presented in FIG. 2. Despite a lack of primary and structural homology, msDNA-Ec67 displays all the unique features found in msDNAs from myxobacteria. These include a single-stranded DNA with a stem-and-loop structure, a single-stranded RNA with a stem-and-loop structure, a 2', 5'-phosphodiester linkage between the RNA and DNA, and a DNA-RNA hybrid at their 3' ends. This hybrid structure was confirmed by demonstrating sensitivity of the RNA molecule to RNaseH.

EXAMPLE 3

Cloning of the locus for msDNA.

Figure 12A:
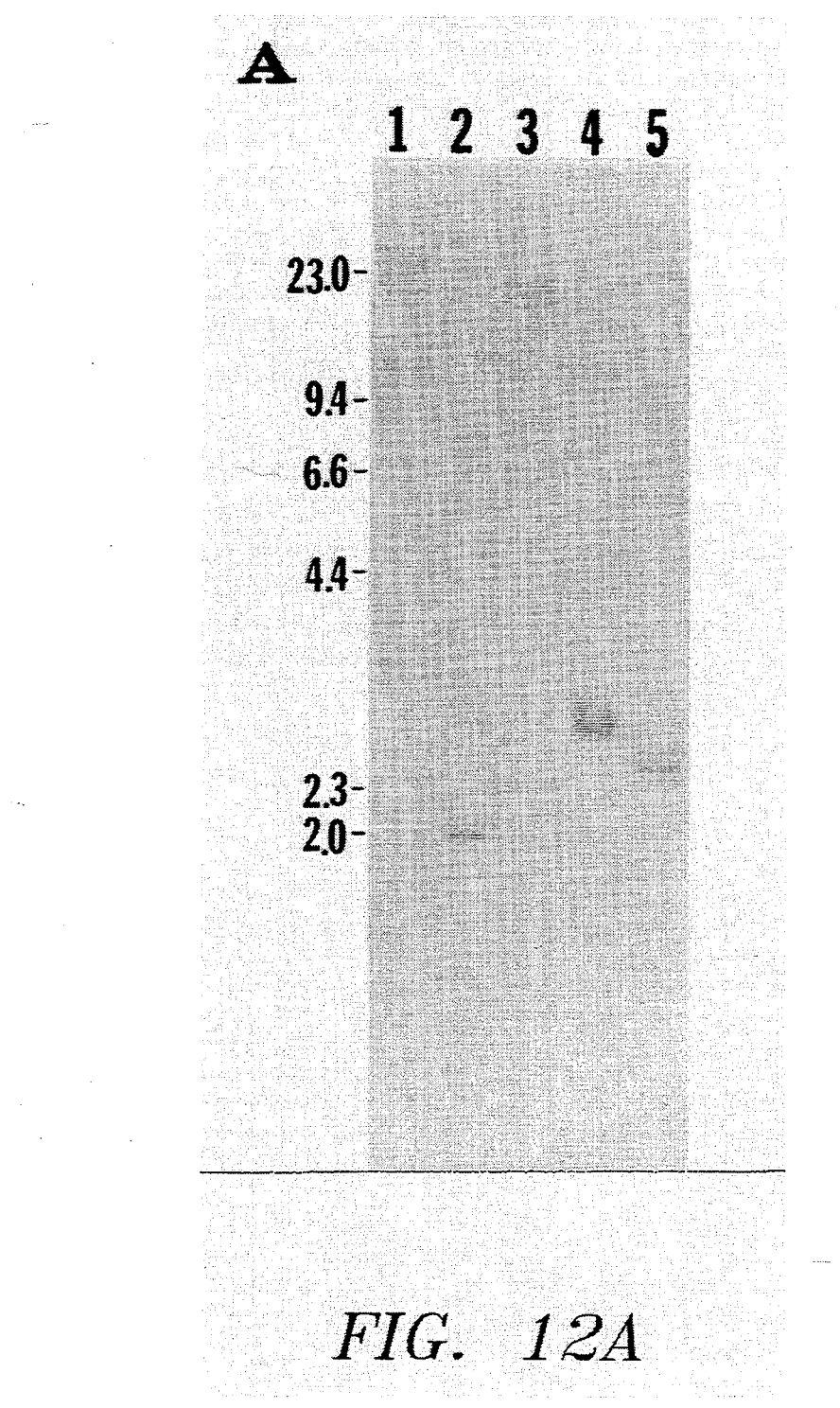
Figure 12B:
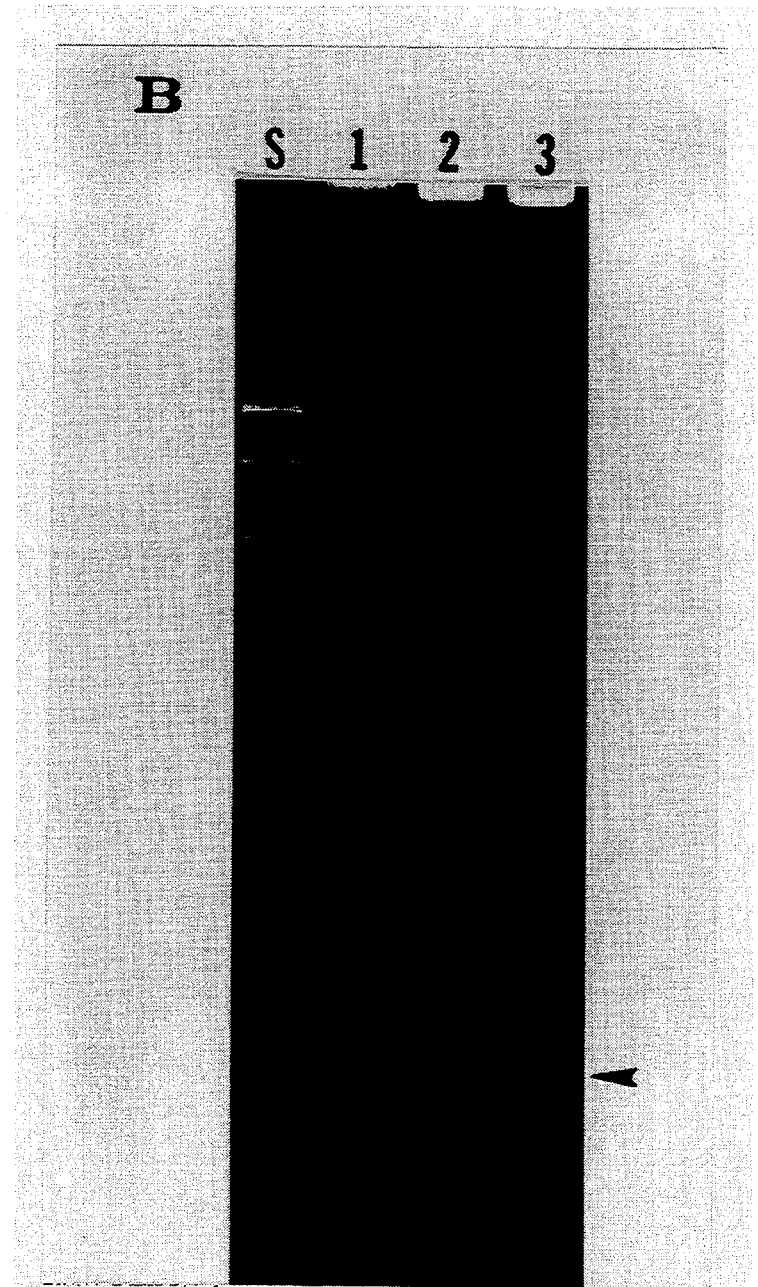

In order to identify the DNA fragment which is responsible for msDNA synthesis in E. coli C1-1, DNA blot hybridization (18) was carried out with various restriction enzyme digests of total chromosomal DNA prepared from *E. coli* C1-1, using msDNA-Ec67 labeled with AMV-RT (the same preparation as shown in lane 3, FIG. 10) as a probe. For each lane, 3 μg of the DNA digest was applied to a 0.7% agarose gel. The result is shown in FIG. 12A EcoRI (lane 1), HindIII (lane 2), BamHI (lane 3), PstI (lane 4) and BglII (lane 5) digestions showed single band hybridization signals corresponding to 11.6, 2.0, approximately 22, 2.8 and 2.5 kilobase pairs (kb), respectively. The upper band appearing in the EcoRI digestion is due to incomplete digestion of the chromosomal DNA. Analysis of total chromosomal DNA prepared form *E. coli* C1-1 by agarose gel electrophoresis revealed that the strain contains two plasmids of different size. However, neither plasmid hybridized with the $^{32}$P-labeled probe, indicating the fragments detected in FIG. 12A are derived from chromosomal DNA. Furthermore, there is only one location for the msDNA-coding region on the chromosome, since various restriction enzyme digestions gave only one band of varying sizes.

The 11.6-kb EcoRI fragment and the 2.8-kb PstI fragment were each cloned into pUC9 (9) and *E. coli* CL83 (a recA transductant of strain JM83), an msDNA-free K-12 strain (lane 1, FIG. 12B) was transformed with the plasmids. Cells transformed with the 11.6-kb EcoRI clone (pC1-1E) were found to produce msDNA (lane 2, FIG. 12B, whereas cells transformed with the 2.8-kb PstI clone (pC1-1P) failed to produce any detectable msDNA (lane 3, FIG. 12B). A map of the 11.6-kb fragment is shown in FIG. 1. DNA blot analysis of the fragment revealed that a 1.8-kb PstI-HindIII fragment hybridized with the msDNA probe. When the DNA sequence of this fragment was determined, a region identical to the sequence of the msDNA molecule was discovered. The DNA sequence corresponding to the sequence of msDNA is indicated by the enclosed box on the lower strand in FIG. 7 and the orientation is from right to left. The location of this sequence is also indicated by a small arrow in FIG. 1. A sequence identical to that of the RNA linked to msDNA (see FIG. 2) was found downstream of the msDNA-coding region in opposite orientation and overlapping with the region by 7 bases. This sequence is indicated by the enclosed box on the upper strand in FIG. 13 and the branched G residue is circled. Again, as in all the msDNAs found in myxobacteria, there is an inverted repeat comprised of a 13-base sequence immediately upstream of the branched G residue (residue 250 to 262; sequence a2 in FIG. 13) and a sequence at the 3' end shown by an arrow in FIG. 13 (residue 368 to 380; sequence a1). As a result of this inverted repeat, a putative longer primary RNA transcript beginning upstream of the RNA coding region and extending through the msDNA coding region would be able to self-anneal and form a stable secondary structure, which is proposed to serve as the primer as well as the template for the msDNA synthesis (5).

EXAMPLE 4

Construction of Synthetic msDNA

Figure 5:
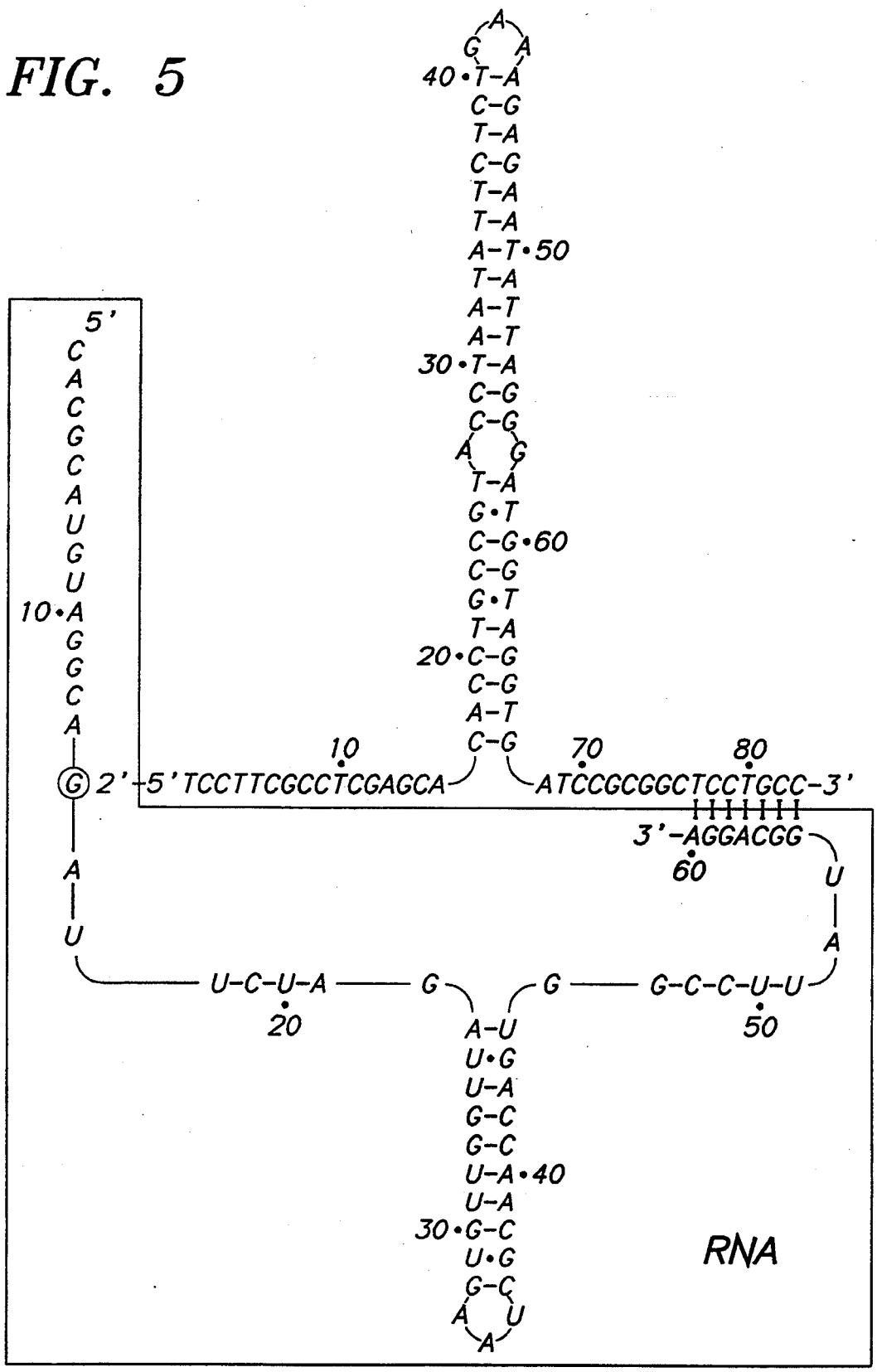
FIG. 5 shows synthetic msDNA ms100.

Two distinct synthetic msDNA molecules were constructed. A 196-bp synthetic msDNA containing an entire msr-msd region was synthesized from four double-stranded oligonucleotide units. The synthetic genes and their components are shown in FIG. 3. Eight single-stranded oligonucleotides, forty-six to fifty-six bases in length were synthesized. The appropriate pairs of oligonucleotides were annealed by heating at 100° C. for 5 minutes, then cooling at 30° C. for 30 minutes and for 30 minutes in a refrigerator. An *E. coli* pINIII(lpp$^{p-}$5) expression vector (14) was digested with XbaI-EcoRI and an XbaI-EcoRI fragment from the clinical *E. coli* strain C1-1 was inserted such that the RT gene under lpp-lac promoter control and used to transform *E. coli*. After identification of the clone, the 10.7-kb pINIII(lpp$^{p-5}$) Ec67-RT plasmid DNA was isolated. The 196-bp synthetic msDNA fragment was then inserted into the vector by digesting with XbaI, treating the vector ends with bacterial alkaline phosphatase and ligating the fragment into the site. The construction scheme is shown in FIG. 4. *E. coli* CL-83 was transformed with the pINIII(lpp$^{p-5}$) ms100-RT plasmid and the production of msDNA determined as in Example 1. The results indicated that msDNA was produced. This artificial msDNA was designated ms100 and is illustrated in FIG. 5.

Figure 6:
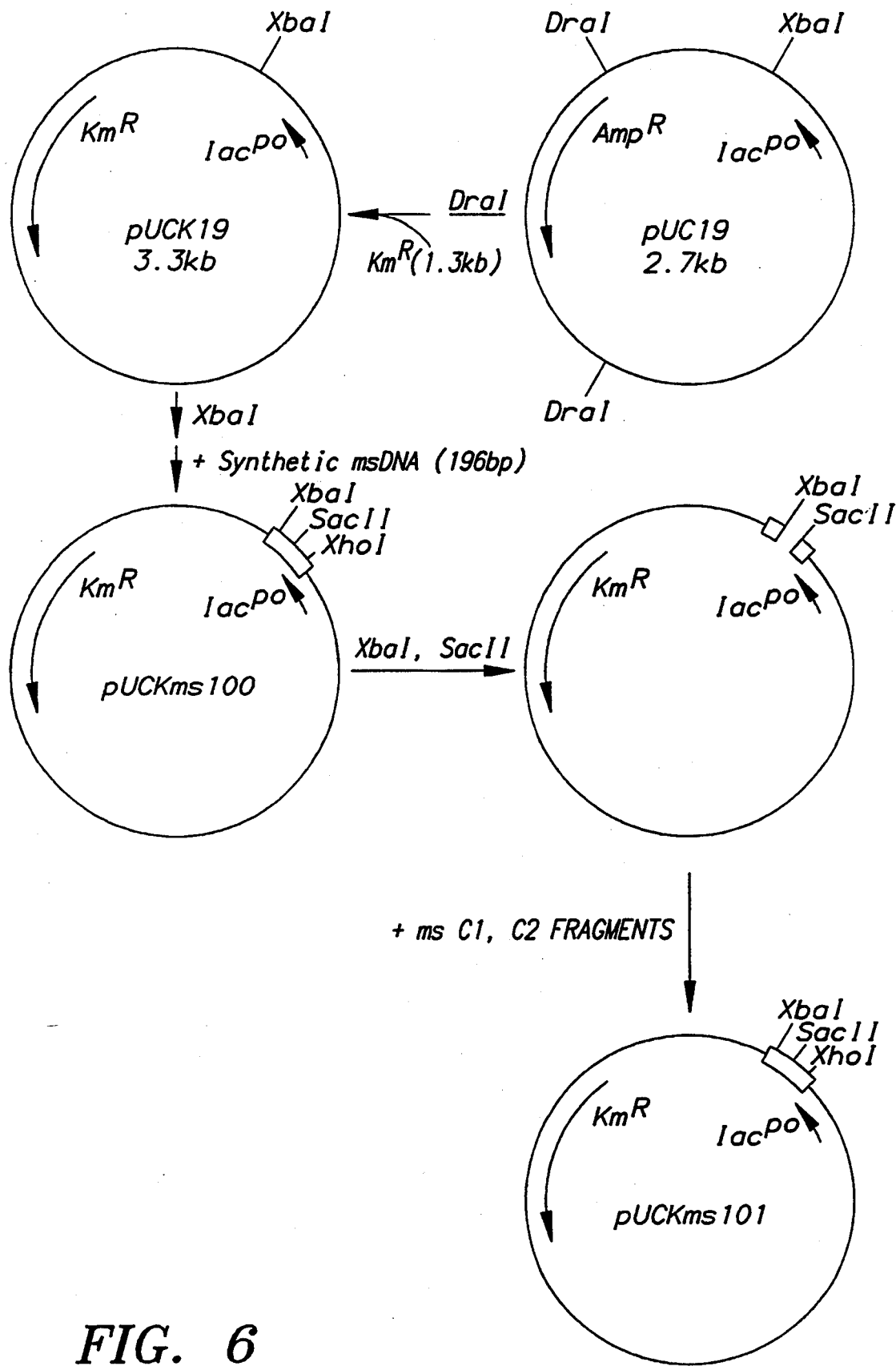
FIG. 6 shows the construction scheme for pUCKms100 and pUCKms101.
Figure 7:
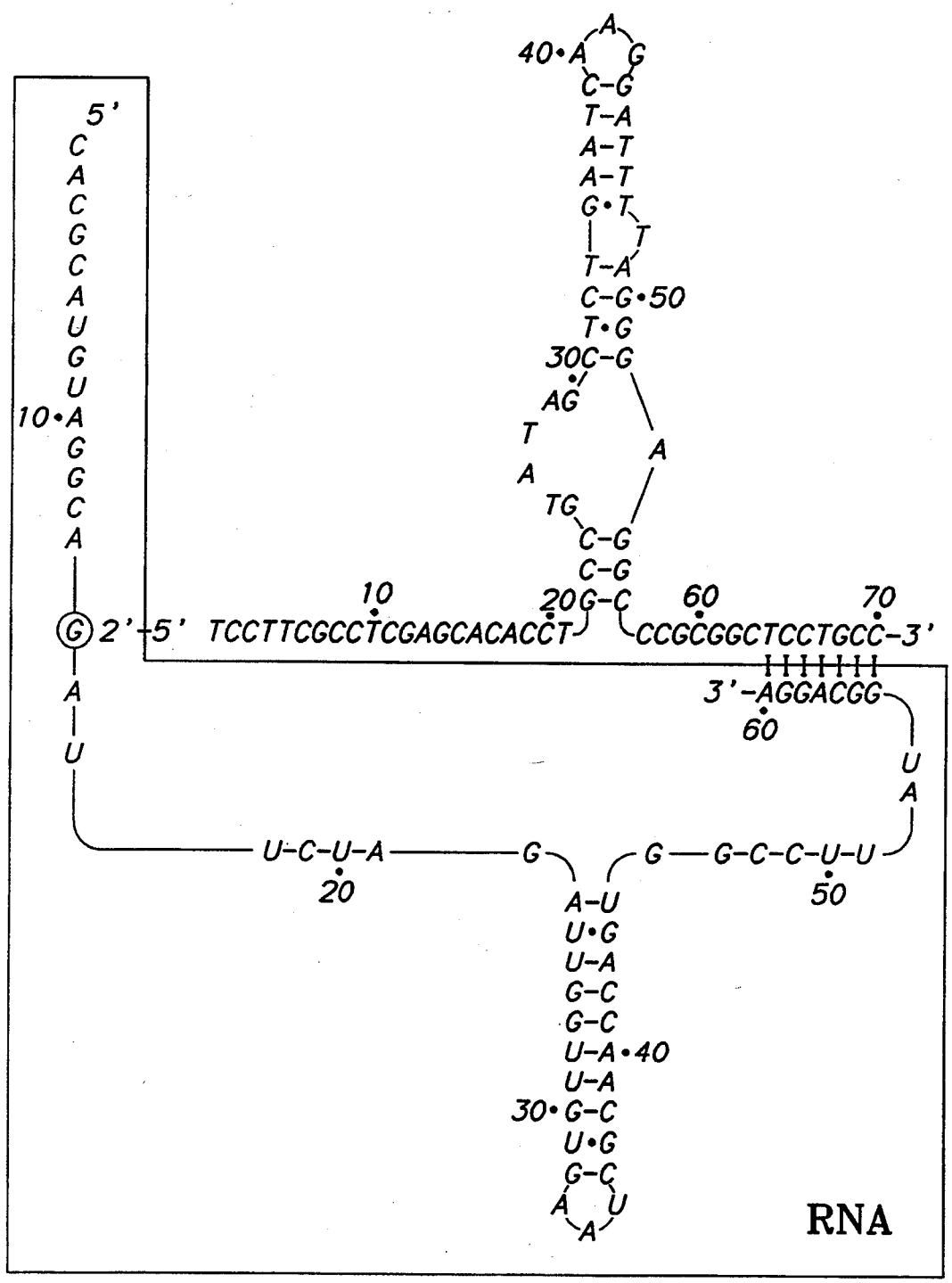
FIG. 7 shows synthetic msDNA ms101.

A second synthetic msDNA, ms101, was expressed from the vector pUCK19, a derivative of pUC19 (13). pUC19 DNA was digested with DraI and the 2-kb fragment isolated. The isolated fragment was ligated to a 1.3-kb HinfI fragment from Tn5 encoding the kanamycin resistance gene. The resultant 3.3-kb plasmid, pUCK19, was digested with XbaI and the 196-bp synthetic msDNA described above was inserted. The pUCKms100 construct was digested with XhoI and SacII which results in the excision of a 61-bp fragment from within the ms100 region. A synthetic 45-mer double-stranded oligonucleotide (shown in FIG. 3B as ms-C1,2) was ligated into the vector yielding pUCKms101 in which the msr-msd region is under lac control. The construction scheme is shown in FIG. 6. RT was provided by transforming *E. coli* containing pUCKms100 or pUCKms101 with plNIII (lpp$^{p-5}$) Ec67-RT. msDNA production was detected in the cells containing these constructs. ms101 is shown in FIG. 7.

EXAMPLE 5

In Vivo cDNA Production in *E. coli*

In order to test a cDNA production in *E. coli*, a plasmid was constructed which was able to produce an mRNA containing a sequence complementary to the 5' end of msDNA-Ec67. The construction of this plasmid (pUC19-Ec67-20), in which a 20-bp sequence was added at the unique XbaI site of pUC19 is illustrated in FIG. 9. The 20-bp sequence contains a 15-base sequence identical to the 3' end of msDNA-Ec67 (see FIG. 2A) so that the RNA transcript from the lac promoter of pUC19 contains the 15-base sequence complementary to the 3' end of msDNA-Ec67 at the position 80 bases downstream of the 5' end of the transcript.

Figure 2A:
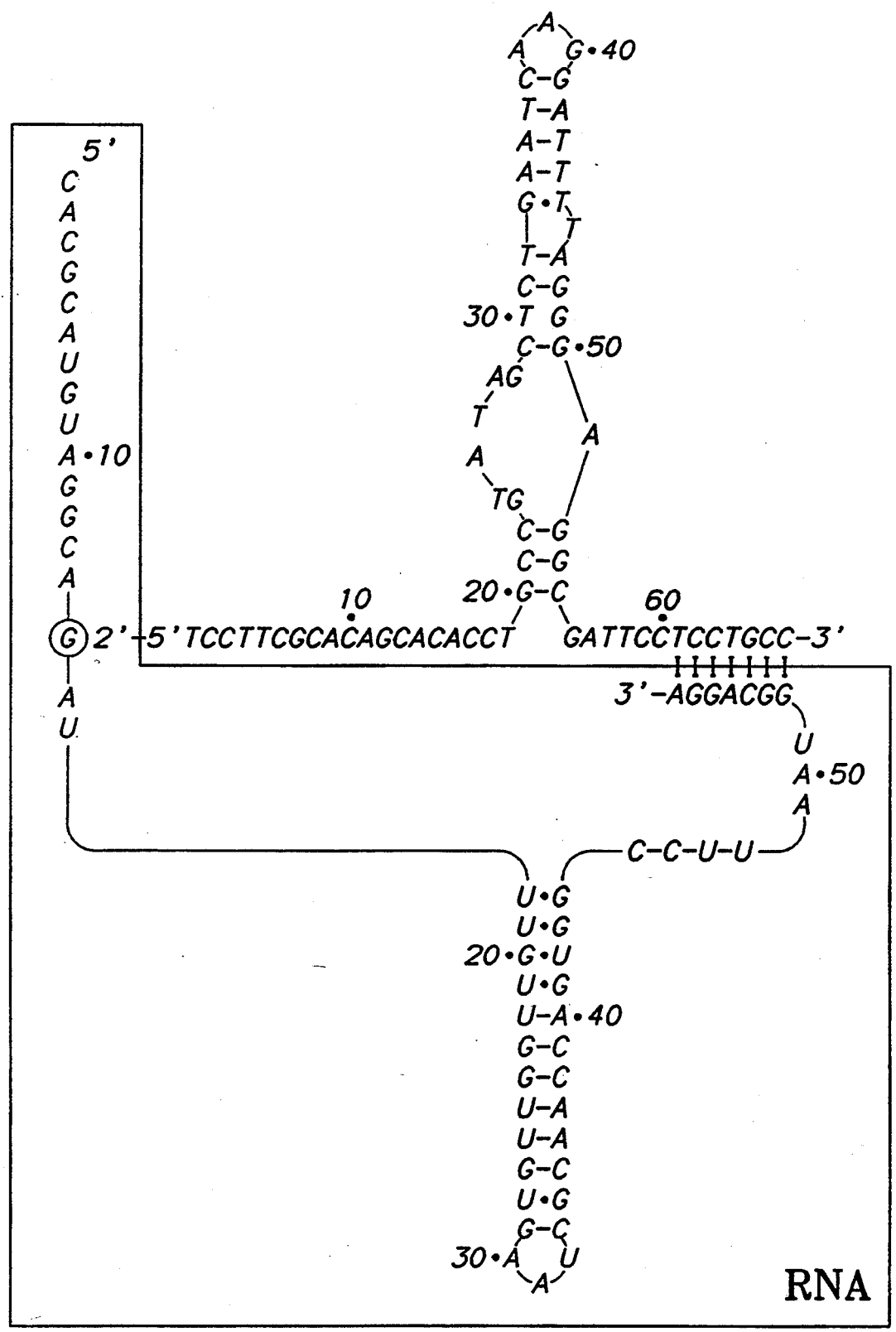
FIGS. 2A and 2B show the complete primary and proposed secondary structure of msDNA-Ec67 and msDNA-Ec74.
Figure 2B:
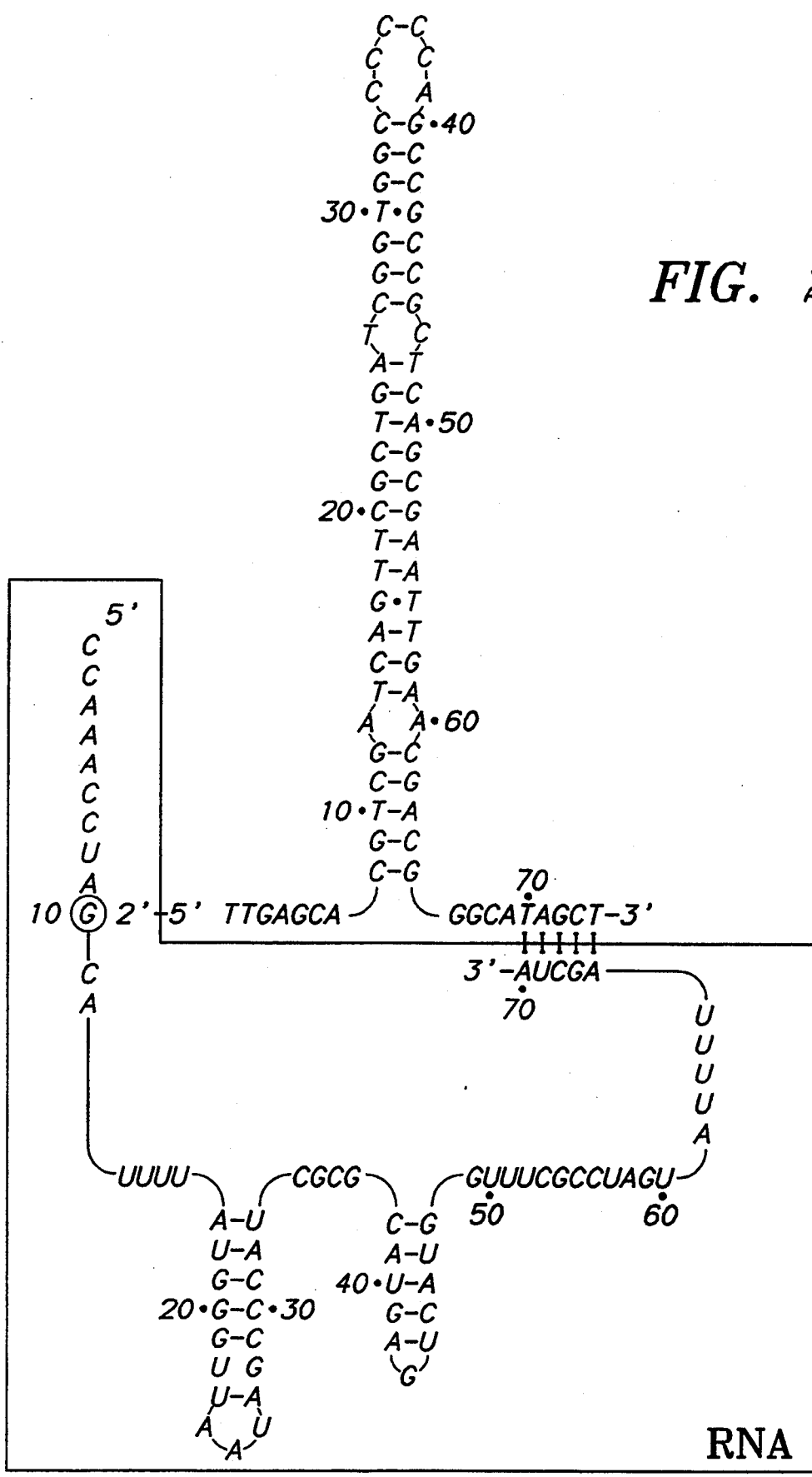

If *E. coli* JA221 harboring the Ec67 retron (pC1-IEP5b), is transformed with plasmid pUC19-Ec67-20, the 3'-end region of msDNA-Ec67 may form a DNA-RNA hybrid not only with the 3' end of msdRNA (as shown in FIG. 2A) but also with the RNA transcript (lacZ mRNA) from pUC19-Ec67-20 as shown in FIG. 9. Since the cells contain Ec67-RT, this enzyme may then start to synthesize cDNA by extending the 3' end of msDNA along the mRNA template. This would produce a single-stranded DNA of 152 bases which consists of the 67-base msDNA at the 5' end and the 85-base cDNA (to the 5' end of the lac transcript; 80 bases from the lacZ mRNA plus 5 bases from the linker)

at the 3' end. Identification of this cDNA was carried out by the polymerase chain reaction (PCR) (19) using a 23-base oligonucleotide complementary to the 3' end of the cDNA (P1; see FIG. 9) and a 23-base oligonucleotide identical to the 5' end of msDNA-Ec67 (P2) as primers. A DNA fraction containing cDNA was digested with ribonuclease A and then used for the PCR. After the 25th cycle of the PCR, the DNA products were fractionated on a 5% polyacrylamide gel and detected by staining with ethidium bromide. A distinct band appeared at the position of approximately 150-base pairs. This band yielded two bands of approximately 80 and 70-base pairs after XbaI, PstI and HindIII digestion. This is in good agreement with the predicted 152-bp cDNA depicted in FIG. 9, which is expected to yield two fragments of 80 and 72-bp upon XbaI digestion. The PCR did not yield any specific bands when pUC19 without the 20-bp insert was used.

FIG. 13 shows nucleotide sequence of the region from the E. coli Cl-1 chromosome encompassing the msDNA and the msdRNA coding regions and an ORF downstream of the msdRNA region. The entire upper strand beginning at the BalI site and ending just beyond the ORF is shown. Only a part of the complementary lower strand is shown from base 241. to 420. The long boxed region of the upper strand (249-306) corresponds to the sequence of the branched RNA portion of the msDNA molecule. The boxed region of the lower strand corresponds to the sequence of the DNA portion of msDNA. The starting site for DNA and RNA and the 5' to 3' orientation are indicated by large open arrows. The msdRNA and msDNA regions overlap at their 3' ends by 7 bases. The circled G residues at position 263 represents the branched rG of RNA linked to the 5' end of the DNA strand in msDNA. Long solid arrows labeled a1 and a2 represent inverted repeat sequences proposed to be important in the secondary structure of the primary RNA transcripts involved in the synthesis of msDNA. Note that the nucleotide at position. 257 (U on the RNA transcript) and the nucleotide at position 373 (G on the RNA transcript) form an U-G pair in the stem between sequence a1 and a2. The proposed promoter elements (−10 and −35 regions) for the primary RNA transcript are also boxed. The ORF coding for 586 amino acid residues begins with the initiation codon ATG at base 418–420 to end with nucleotide 2175. Single letter designations are given for amino acids. The YXDD amino acid sequence conserved among known RT proteins is boxed. Numbers on the right hand column enumerate the nucleotide bases and numbers with a * enumerate amino acids. Small vertical arrows labelled H and P locate the HindIII and PstI restriction cleavage sites, respectively. The DNA sequence was determined by the chain termination method using synthetic oligonucleotides as primers.

REFERENCES

1. Yee, T. et al., Cell 38, 203 (1984).
2. Dhundale, A. et al., Cell 51, 1105 (1987).
3. Furuichi, T. et al., Cell 48, 47 (1987).
4. Furuichi, T. et al., Cell 48, 55 (1987).
5. Dhundale, A. et al., J. Bacteriol. 164, 914 (1985).
6. Dhundale, A. et al., J. Biol. Chem. 263, 9055 (1988).
7. Lira, D. and Maas, W., Cell 56, 891 (1989).
8. Temin, H. M., Nature 339, 254 (1989).
9. Lampson, B. C. et al., Science 243, 1033 (1989).
10. Maxam, A. M. and Gilbert, W., Methods Enzymol. 65, 499 (1980).
11. Ruskin, B. and Green, M., Science 229, 135 (1985).
12. Arenas, J. and Hurwitz, J., J. Biol. Chem. 262, 4274 (1987).
13. Yanisch-Perron, Y. et al., Gene 33, 103 (1985).
14. Masui, Y. et al., "Experimental Manipulation of Gene Expression" ( ed. M. Inouye), pp. 15–32, Academic Press, New York (1983).
15. Hutchins, C. J. et al., Nucl. Acids Res. 14, 3627 (1986).
16. Foster, A. C. and Symons, R. H., Cell 49, 211 (1987).
17. Coleman, J. et al., Cell 37, 429 (1984).
18. Southern, E., J. Mol. Biol. 98, 503 (1975).
19. Saiki, R. K. et al., Science 230, 1350 (1985).

We claim:

1. A plasmid which comprises a retron which encodes a msDNA molecule selected from the group consisting of Ec67, Ec74, ms100 and ms101, which has a DNA and an RNA portion, which retron comprises an msd gene, an msr gene and an open reading frame (ORF), the msd gene coding for the DNA strand of the msDNA molecule and the msr gene coding for the RNA strand of the msDNA molecule, the msr gene overlapping with and in opposite orientation with respect to the msd gene and the ORF coding for a reverse transcriptase (RT), said RT synthesizing cDNA from an RNA transcript into the msDNA molecule.

2. The plasmid of claim 1 wherein the msDNA molecule is Ec67.

3. The plasmid of claim 1 wherein the msDNA molecule is Ec74.

4. The plasmid of claim 1 wherein the msDNA molecule is ms100.

5. The plasmid of claim 1 wherein the msDNA molecule is ms101.

6. The plasmid of claim 1 wherein the msDNA molecule contains a foreign DNA fragment positioned in an antisense orientation in the RNA or the DNA portion of the msDNA molecule.

7. The plasmid of claim 6 wherein the msDNA molecule is ms100.

8. The plasmid of claim 6 wherein the msDNA molecule is ms101.

9. A prokaryote transformed with the plasmid of claim 1.

10. The prokaryote of claim 9 which is a bacterium.

11. The bacterium of claim 10 which is E. coli.

12. An isolated retron which encodes a hybrid DNA/RNA msDNA molecule selected from the group consisting of Ec67, Ec74, ms100 and ms101, which has a DNA and an RNA portion, which retron comprises an msd gene, an msr gene and an open reading frame (ORF), the msd gene coding for the DNA strand of the msDNA molecule and the msr gene coding for the RNA strand of the msDNA molecule, the msr gene overlapping with and in opposite orientation with respect to the msd gene and the ORF coding for a reverse transcriptase (RT), said RT synthesizing cDNA from an RNA transcript of the retron which encodes the msDNA molecule.

13. The retron of claim 12, wherein the msr and msd genes are synthetic.

14. The retron of claim 13 which codes for the ms100 msDNA molecule.

15. The retron of claim 12 wherein the ORF is located upstream of the msd and downstream of the msr.

16. The retron of claim 15, wherein the ORF is from a source different than the msr and msd genes.

17. The retron of claim 15 wherein the RT has 586 amino acid residues.

18. The retron of claim 12 which codes for the Ec67 msDNA molecule.

19. The retron of claim 12, wherein a foreign nucleic acid sequence is positioned in the gene selected from the group consisting of the msr and msd genes.

20. The retron of claim 12 which codes for the Ec74 msDNA molecule.

21. The retron of claim 12 which codes for the ms101 msDNA molecule.

22. The retron of claim 12 wherein the msDNA molecule contains a foreign DNA fragment positioned in an antisense orientation in the RNA or the DNA portion of the msDNA molecule.

23. The retron of claim 22 wherein the msDNA molecule is ms100.

24. The retron of claim 22 wherein the msDNA molecule is ms101.

25. An isolated msDNA molecule selected from the group consisting of Ec67, Ec74, ms100 and ms101.

26. The msDNA of claim 25 which is the synthetic ms100.

27. The msDNA of claim 25 which is Ec67.

28. The msDNA of claim 25 which is Ec74.

29. The msDNA of claim 25 which is the synthetic ms101.

* * * * *

UNITED STATES PATENT AND TRADEMARK OFFICE
CERTIFICATE OF CORRECTION

PATENT NO.     : 5,405,775
DATED          : April 11, 1995
INVENTOR(S)    : Inouye et al.

It is certified that error appears in the above-identified patent and that said Letters Patent is hereby corrected as shown below:

Column 1,
Line 26, before "FIELD OF THE INVENTION" please insert the following paragraph:

-- The U.S. Government has a paid-up license in this invention and the right in limited circumstances to require the patent owner to license others on reasonable terms as provided for by the terms of Grant No. GM44012 awarded by the NIH. --

Signed and Sealed this

Ninth Day of September, 2003

JAMES E. ROGAN
*Director of the United States Patent and Trademark Office*